US012298037B2

(12) United States Patent
Pisharodi

(10) Patent No.: US 12,298,037 B2
(45) Date of Patent: May 13, 2025

(54) SYSTEM FOR DELIVERY OF INACTIVATED PATHOGENS FOR CONTACTLESS PASSIVE IMMUNIZATION

(71) Applicant: Madhavan Pisharodi, Brownsville, TX (US)

(72) Inventor: Madhavan Pisharodi, Brownsville, TX (US)

(73) Assignee: PERUMALA HOLDINGS, LLC, Brownsville, TX (US)

( * ) Notice: Subject to any disclaimer, the term of this patent is extended or adjusted under 35 U.S.C. 154(b) by 0 days.

(21) Appl. No.: 18/407,208

(22) Filed: Jan. 8, 2024

(65) Prior Publication Data

US 2024/0142124 A1 May 2, 2024

Related U.S. Application Data

(63) Continuation-in-part of application No. 18/328,463, filed on Jun. 2, 2023, now Pat. No. 12,194,206, and a continuation-in-part of application No. 18/058,185, filed on Nov. 22, 2022, now Pat. No. 11,951,164, said application No. 18/328,463 is a continuation-in-part of application No. 18/058,185, filed on Nov. 22, 2022, now Pat. No. 11,951,164, which is a continuation-in-part of application No. 17/545,822, filed on Dec. 8, 2021, now Pat. No. 11,511,013.

(60) Provisional application No. 63/479,143, filed on Jan. 9, 2023, provisional application No. 63/233,697, filed on Aug. 16, 2021.

(51) Int. Cl.
*F24F 8/22* (2021.01)
*F24F 13/06* (2006.01)

(52) U.S. Cl.
CPC ............... *F24F 8/22* (2021.01); *F24F 13/06* (2013.01)

(58) Field of Classification Search
None
See application file for complete search history.

(56) References Cited

U.S. PATENT DOCUMENTS

| | | |
|---|---|---|
| 3,721,072 A | 3/1973 | Miller |
| 3,773,044 A | 11/1973 | Wallace |
| 3,850,170 A | 11/1974 | Cox |
| 4,580,556 A | 4/1986 | Kondur |
| 4,742,760 A | 5/1988 | Horstman |
| 5,656,242 A | 8/1997 | Morrow et al. |
| 7,185,510 B2 | 3/2007 | Lee et al. |
| 8,336,821 B2 | 12/2012 | Shell et al. |
| 8,674,322 B2 | 3/2014 | Kohler |
| 11,052,169 B1 | 7/2021 | Pisharodi |
| 2006/0057020 A1 | 3/2006 | Tufo |
| 2006/0263276 A1 | 11/2006 | Pattee |
| 2008/0112845 A1 | 5/2008 | Dunn |
| 2008/0173178 A1 | 7/2008 | Metteer |
| 2010/0150793 A1 | 6/2010 | Chan |
| 2011/0286167 A1 | 11/2011 | Winkler |
| 2012/0128539 A1* | 5/2012 | Gross ............... F24F 8/192 422/121 |
| 2012/0301363 A1 | 11/2012 | Kim et al. |
| 2016/0001108 A1 | 1/2016 | Zhou et al. |
| 2017/0341762 A1 | 11/2017 | Breigenzer |
| 2018/0250430 A1 | 9/2018 | Machovina et al. |
| 2019/0009912 A1 | 1/2019 | Matsui |
| 2020/0155667 A1* | 5/2020 | James ............... A61K 39/12 |

FOREIGN PATENT DOCUMENTS

WO  WO-2022090586 A1 * 5/2022

OTHER PUBLICATIONS

Translation of WO-2022090586-A1 (Year: 2022).*
'How a packaged system works' (Goodman) Jul. 29, 2016, [online] retrieved from <URL: https://web.archive.org/web/20160729193422/https://www.goodmanmfg.com/resources/heating-cooling-101/how-a-packaged-system-works>.
Hankaniemi etal., Vaccine, vol. 37, Issue 40, pp. 5962-5971, (Year: 2019).
'UVC disinfects SARS CoV 2 by induction of viral genome damage without apparent effects on viral morphology and proteins' (Lo) Jul. 5, 2021, [online] retrieved from <URL: https://doi.org/10.1038/s41598-021-93231-7>.
'UV Inactivation of Rotavirus and Tulane Virus Targets Different Components of the Virions' (Araud) Feb. 3, 2020, [online] retrieved from <URL: https://doi.org/10.1128/AEM.02436-19.>.
W. C. Russell; "Adenoviruses: update on structure and function;" Journal of General Virology (2009), 90, 1-20; DOI 10.1099/vir.0.003087-0.
'Ultraviolet A light effectively reduces bacteria and viruses including coronavirus' (Rezale) Jul. 16, 2020, [online] retrieved from <URL: https://doi.org/10.1371/journal.pone.0236199>.
Koma T, Doi N, Suzuki A, Nagamatsu K, Yasui T, Yasutomo K, Adachi A, Minamikawa T and Nomaguchi M (2022) Major target for UV-induced complete loss of HIV-1 infectivity: A model study of single stranded RNA enveloped viruses. Front. Virol. 2:994842. doi: 10.3389/fviro.2022.994842.

(Continued)

*Primary Examiner* — Shanon A. Foley
*Assistant Examiner* — Myron G Hill
(74) *Attorney, Agent, or Firm* — D'Ambrosio & Menon, PLLC; Usha Menon

(57) ABSTRACT

A system for delivering inactivated pathogens to an enclosure includes an air delivery system, the air delivery system comprising: (a) an air intake; (b) an air conditioning unit; (c) an air mover; (d) a UVC disinfection unit; (e) an enclosure; (f) an enclosure air entry vent; (g) an enclosure air discharge vent; and (h) an air circulation pathway going from the air intake through an air duct connected at one end to the air intake and at a second end to the enclosure air entry vent that opens into the enclosure, wherein the air duct provides a passageway through the air delivery system. A pathogen loading inlet is connected to the air circulation pathway. The enclosure is a room, a nursing home, an airplane, a train, a ship, or a critical care unit in a hospital. The enclosure can also be a free-standing and/or mobile unit.

9 Claims, 11 Drawing Sheets

(56) References Cited

OTHER PUBLICATIONS

'UV C irradiation is highly efective in inactivating SARS CoV 2 replication' (Biasin) Mar. 18, 2021, [online] retrieved from <URL: https://doi.org/10.1038/s41598-021-85425-w>.

Eischeid, Anne C. et al; "Molecular Indications of Protein Damage in Adenoviruses after UV Disinfection;" Applied and Environmental Microbiology, Feb. 2011, p. 1145-1147 vol. 77, No. 3.

Araud E, Fuzawa M, Shisler JL, Li J, Nguyen TH. 2020. UV inactivation of rotavirus and Tulane virus targets different components of the virions. Appl Environ Microbiol 86:e02436-19. https://doi.org/10.1128/AEM 02436-19.

Ma B, Gundy PM, Gerba CP, Sobsey MD, Linden KG. 2021. UV inactivation of SARSCoV-2 across the UVC spectrum: KrCl* excimer, mercury-vapor, and light-emitting-diode (LED) sources. Appl Environ Microbiol 87: e01532-21. https://doi.org/10.1128/AEM.01532-21.

Christin Scheller; "Physicochemical properties of SARS-CoV-2 for drug targeting, virus inactivation and attenuation, vaccine formulation and quality control" Electrophoresis 2020, 41, pp. 1137-1151; Wiley-VCH Verlag Gmbh & Co. KGaA.

George Devitt et al; "Mechanisms of SARS-CoV-2 Inactivation using UVC Laser Radiation" bioRxiv preprint Feb. 3, 2023.; https://doi.org/10.1101/2023.02.03.526944doi.

Ernest R. Blatchley, III et al; "SARS-CoV-2 Ultraviolet Radiation Dose-Response Behavior" SARS-CoV-2 Ultraviolet Radiation Dose-Response Behavior; Journal of Research of the National Institute of Standards and Technology; vol. 126, Article No. 126018 (2021) https://doi.org/10.6028/jres.126.018.

Ernest R. Blatchley, III et al; "Far UV-C Radiation: Current State-of Knowledge" International Ultraviolet Association; Whitepaper of The IUVA Task Force (TF) on Far UV-C Radiation for Disinfection of Air and Surfaces; May 14, 2021. https://iuva.org/Projects-Articles-Repository/10503221.

Beck, Sara E. et al. "Wave-length dependent Damage to Adenoviral Proteins Across the Germacidal UV Spectrum" Environ. Sci. Technol. 2018, 52, 223-229.

Joshua Hadi et al; "Control Measures for SARS-CoV-2: A Review on Light-Based Inactivation of Single-Stranded RNA Viruses" Pathogens 2020, 9, 737; doi:10.3390/pathogens9090737; http://www.mdpi.com/journal/pathogens.

Sanjeev K. Bhardwaj et al "UVC-based photoinactivation as an efficient tool to control the transmission of coronaviruses" Science of the Total Environment 792 (2021) 148548; www.elsevier.com/locate/scitotenv.

Loveday, E.K.; Hain, K.S.; Kochetkova, .; Hedges, J.F.; Robison, A.; Snyder, D.T.; Brumfield, S.K.; Young, M.J.; Jutila, M.A.; Chang, C.B.; et al. Effect of Inactivation Methods on SARS-CoV-2 Virion Protein and Structure. Viruses 2021, 13, 562. https://doi.org/10.3390/v13040562.

Naomi Takasuka et al; "A subcutaneously injected UV-inactivated SARS coronavirus vaccine elicits systemic humoral immunity in mice" International Immunology, vol. 16, No. 10, pp. 1423-1430; 2004; The Japanese Society for Immunology; doi:10.1093/intimm/dxh143.

Ong, Q. et al; "Irradiation of UVC LED 277 nm inactives coronaviruses in association to photodegradation of spike protein;" Helion 8 (2022) e11132; www.cell.com/heliyon.

Renata Sesti-Costa et al; "UV 254 nm is more efficient than UV 222 nm in inactivating SARS-CoV-2 present in human saliva;" Photodiagnosis and Photodynamic Therapy 39 (2022) 103015; https://doi.org/10.1016/j.pdpdt.2022.103015.

\* cited by examiner

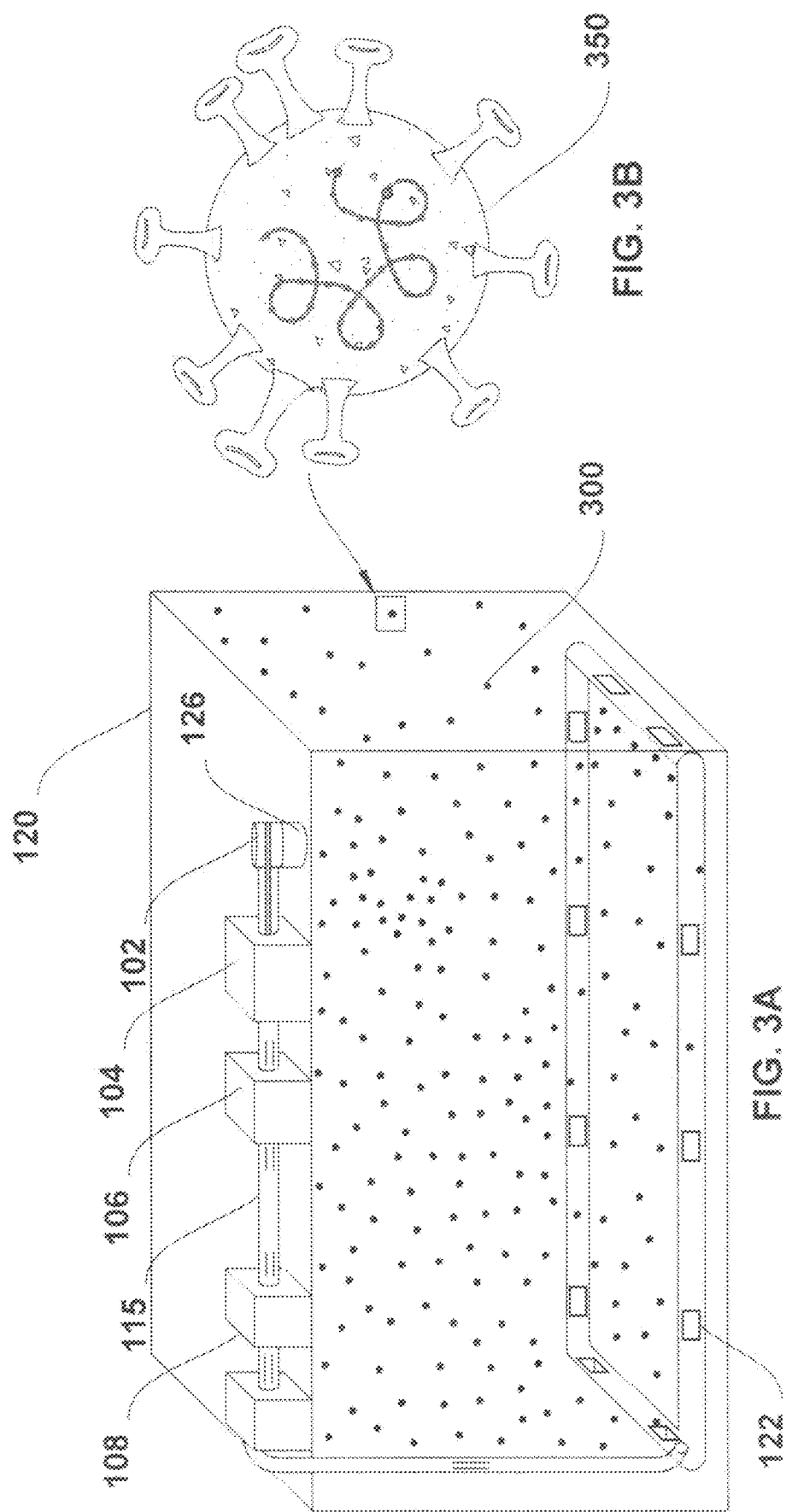

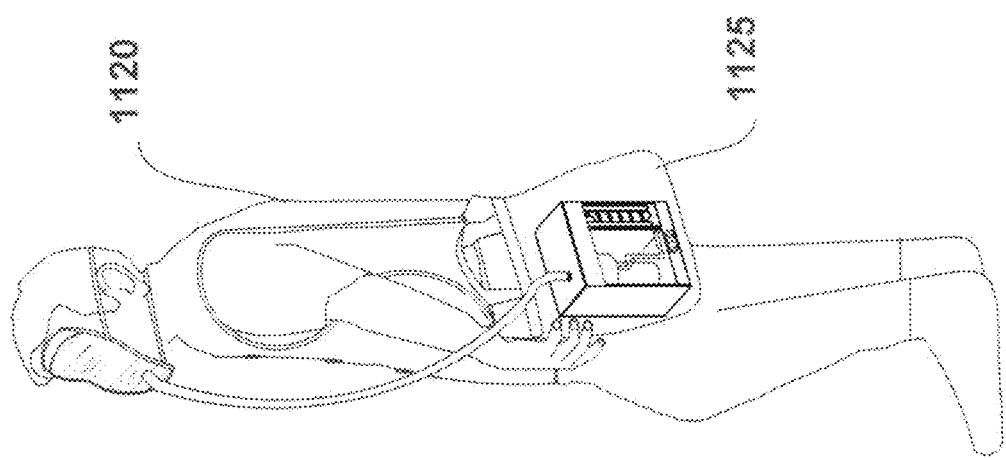
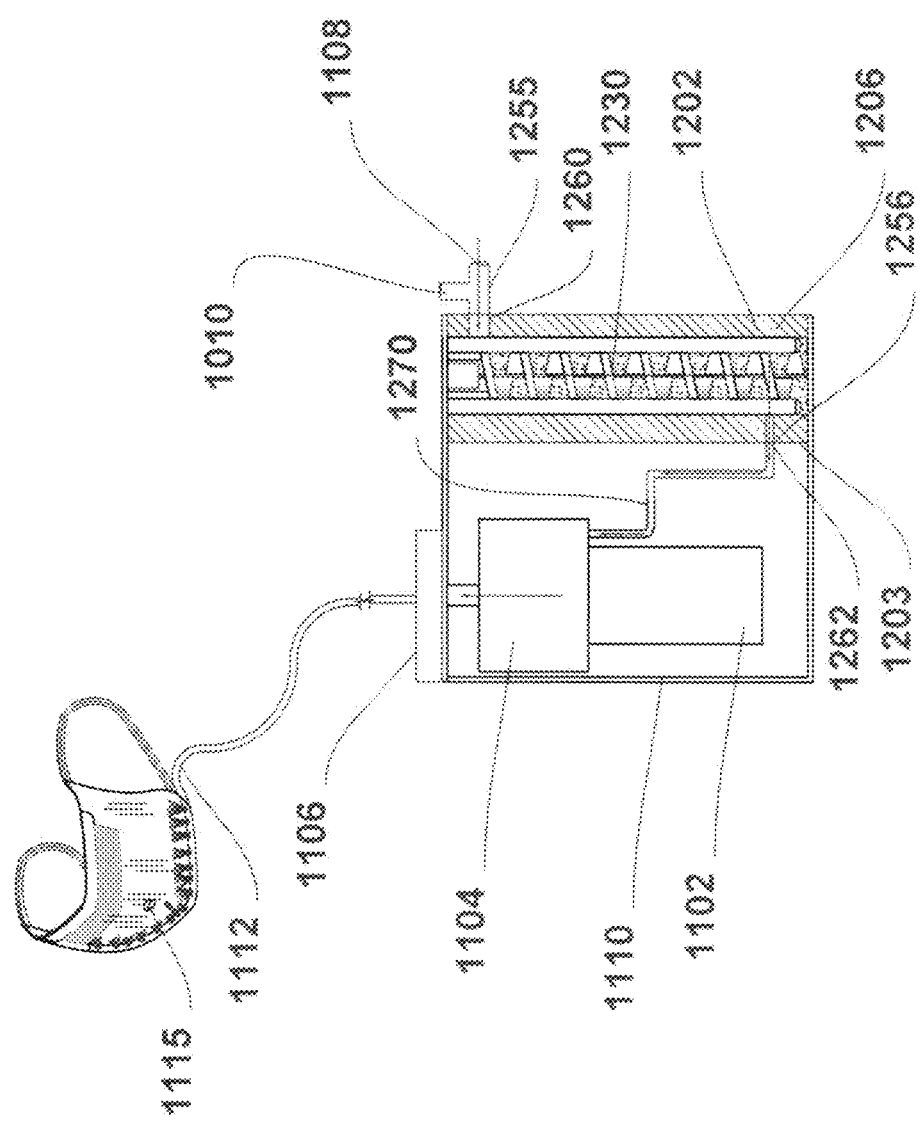

SYSTEM FOR DELIVERY OF INACTIVATED PATHOGENS FOR CONTACTLESS PASSIVE IMMUNIZATION

CROSS REFERENCE TO RELATED APPLICATIONS

This application is a non-provisional application of and claims priority to U.S. Provisional Patent Application Ser. No. 63/479,143 filed on Jan. 9, 2023. This application also claims priority to and is a continuation in part of U.S. Ser. No. 18/328,463 filed on Jun. 2, 2023 and Ser. No. 18/058,185 filed on Nov. 22, 2022. The entire disclosures of these patent applications are part of the disclosure of the present application and are hereby incorporated by reference in their entireties.

FIELD OF THE INVENTION

The present invention relates to a novel method for infection control. In particular, the present invention discloses a novel enclosure with a controlled air flow of air containing an inactivated pathogen for inducing a passive immunity in humans and animals.

BACKGROUND

The background description includes information that may be useful in understanding the present invention. It is not an admission that any of the information provided herein is prior art or relevant to the presently claimed invention, or that any publication specifically or implicitly referenced is prior art.

In the struggle for the humans to fight and survive against the viruses and bacteria which are the original occupants and landlords of our planet, vaccines have played a major role. From the time whole live virus (cowpox in 1796) was used as the vaccine in a quasi-scientific adventure to the present day dealing with extensively thought out and investigated use of SRS-COV-2, S protein subunit vaccines, our struggle to survive and claim our occupancy in this planet has seen many ups and downs. In the process, we have used tamed (attenuated) live viruses, killed (and mutilated) whole virus vaccines, and various forms of subunit vaccines through recombinant (forced marriage) methods. Most of the presently available COVID-19 vaccines belong to this third group. Undoubtedly all three varieties of vaccines have advantages and disadvantages to consider.

Social distancing and the use of personal protective equipment (PPE), such as mask and face shields, have been recommended to protect individuals and control the spread of airborne viruses, such as, SARS-CoV-2 (or the COVID-19) virus. However, these measures may not be sufficient to contain the spread of the COVID-19 virus especially in confined spaces. Most face masks have a questionable ability to block fine virus particles. In infected individuals, the masks block the escape of large virus droplets thus forcing them to breathe in more and more viruses with each breath and reinfect themselves with the viruses they should be expelling. Social distancing is of questionable value in a facility where people move around because the virus droplets take eight minutes or more to drop from a height of five feet. Inevitably, a virus "halo" from the infected person lies in wait for the next person to pass by. Lockdowns have only temporary value because the virus is still present in the ambient air when the lockdown is lifted.

To be effective, the virus has to be destroyed or neutered and the battle should be preferably outside the body since we do not yet know the long-term complications suffered by individuals who are supposedly "cured" of neither the COVID-19 virus nor the long-term effects of current vaccines. Recent studies have found that the COVID-19 virus and other variants spread not only through close personal contacts but also through long distance and for extended periods through the air. Even if the virus droplets fall down within a six-foot radius, the viruses in these droplets are not destroyed. Instead, these droplets dry up, releasing the virus particles of about 0.1 micron to float into the air converting rooms, buildings, airplanes, etc. into something similar to smoke filled facilities. Even an N95 mask cannot block these particles completely.

For example, the COVID-19 virus can infect buildings, airplanes, buses, trains and other structures that have inadequate disinfection functionality in the associated air temperature control system or in air conditioner system with sluggish air movement. Such air conditioner systems can function as a "vector equivalent" for the COVID-19 virus and other microorganisms. Individuals in confined/enclosed spaces are constantly exposed to this deadly virus every time they inhale the air from such an infected building, structure or conventional mask. Neither the air conditioning system nor a conventional mask may be able to protect these individuals because either the masks cannot block such fine virus particles or the masks that can partially block such particles eventually fail due to overloading. Ideally, the air conditioner system can be upgraded to protect against the COVID-19 virus and other microorganisms.

The only long term solution is to develop a multivalent vaccine that can prevent the infection of individuals with the COVID-19 virus. If there are only a few people that become infected with the virus, the virus is unlikely to have a chance to mutate into a strain that can bypass the antibodies created in response to a multivalent vaccine, Therefore, there is an ongoing need to provide better infection control systems and methods.

SUMMARY

One embodiment of the invention is a system for delivering inactivated pathogens to an enclosure comprising an air delivery system. The air delivery system includes: (a) an air intake; (b) an air conditioning unit; (c) an air mover; (d) a UVC disinfection unit; (e) an enclosure; (f) an enclosure air entry vent; (g) an enclosure air discharge vent; and (h) an air circulation pathway going from the air intake through an air duct connected at one end to the air intake and at a second end to the enclosure air entry vent that opens into the enclosure, where the air duct provides a passageway through the air delivery system. The air mover can control the velocity of air movement through the air duct.

In one or more embodiments, the UVC disinfection unit comprises a housing that encloses a disinfection chamber that has: (a) a chamber wall; (b) a chamber inlet; (c) a chamber outlet; (d) a centralized inner bore having an interior chamber surface facing the inner bore; (e) a UVC light source positioned adjacent the interior chamber surface; and (f) a helical air flow diverter centralized within the inner bore proximal the UVC light source, wherein the helical airflow diverter creates a helical path for the air circulation pathway to proceed through the disinfection chamber from the chamber inlet to the chamber outlet.

The air disinfection unit can contain more than one UVC disinfection chamber.

The enclosure can be a room, a nursing home, an airplane, a train, a ship, or a critical care unit in a hospital. In one or more embodiments, the enclosure can be configured as a free-standing and/or mobile/transportable enclosure.

The system can have a pathogen loading inlet connected to the air circulation pathway. In another embodiment, the system can have a test chamber connected to the air circulation pathway adjacent the UVC disinfection unit. In one or more embodiments, the system is configured as a contactless system for immunizing humans, birds or animals.

Another embodiment of the invention is a personal immunization device comprising: (a) an air disinfection unit having an air disinfection chamber within a UV impenetrable housing, an air mover, and a power unit; and (b) a face mask. The UV impenetrable housing has an air inlet and an air outlet separated by the air disinfection chamber. The personal immunization device can include a pathogen loading site attached to the air inlet. The air mover can control the velocity of air movement through the device. The air disinfection unit can have a housing that is opaque to UVC. The air mover moves air from the pathogen loading site, through the air disinfection unit, and into the face mask.

The personal immunization device can have a test chamber positioned between the air disinfection unit and the face mask.

The air disinfection chamber comprises: (a) a chamber wall that is transparent to UVC light; (b) a chamber inlet; (c) a chamber outlet; (d) a centralized inner bore having an interior chamber surface facing the inner bore; (e) a UVC light source positioned adjacent the interior surface; and (f) a helical air flow diverter centralized within the inner bore proximal the UVC light source, wherein the helical airflow diverter creates a helical path for the airflow pathway as the airflow pathway proceeds from the housing inlet to the housing outlet.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The invention will be described in further detail below and with reference to the attached drawings, which describe or relate to methods and devices of the present invention.

FIG. 3A illustrates one embodiment of the air delivery system shown in FIG. 1 with a pathogen laden air circulating within an embodiment of an enclosure.

FIG. 3B is a schematic illustration of a SARS-COV-2 as an example of a pathogen represented in FIG. 2B.

FIG. 10A illustrates one embodiment of a personal protective biological device with a virus intake port attached to the external air intake port.

FIG. 10B illustrates a person wearing the embodiment of the personal protective biological device illustrated in FIG. 10A.

DETAILED DESCRIPTION

Figure 1:
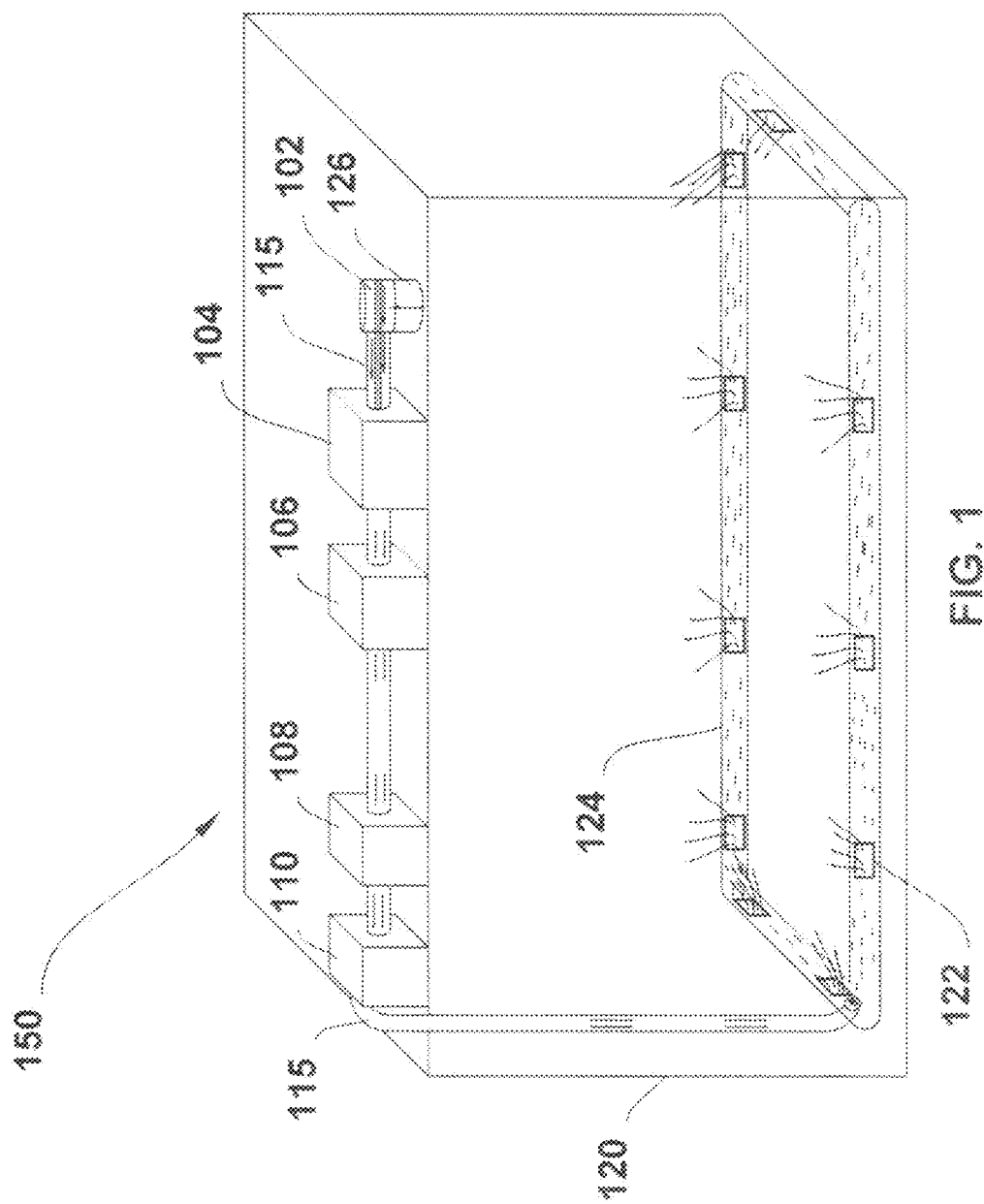
FIG. 1 illustrates one embodiment of an air delivery system.

Characteristics and advantages of the present disclosure and additional features and benefits will be readily apparent to those skilled in the art upon consideration of the following detailed description of exemplary embodiments. The intention is to cover all modifications, equivalents and alternatives falling within the spirit and scope of this disclosure. Many changes may be made to the particular embodiments and details disclosed herein without departing from such spirit and scope. For instance, although SARS-COV-2 virus is used as an example of the invention, it is understood that the methods and devices disclosed herein can be used for other viruses and human and mammalian pathogens.

The present invention relates to a novel method for infection control. In particular, the present invention discloses a novel immunization method using a novel aerosolized neutered pathogenic source.

Characteristics and advantages of the present disclosure and additional features and benefits will be readily apparent to those skilled in the art upon consideration of the following detailed description of exemplary embodiments. It should be understood that the description herein, being of example embodiments, is not intended to limit the claims of this patent (or any patent claiming priority hereto). On the contrary, the intention is to cover all modifications, equivalents and alternatives falling within the spirit and scope of this disclosure and the appended claims. Many changes may be made to the particular embodiments and details disclosed herein without departing from such spirit and scope. For instance, although SARS-COV-2 is often used as an example of the invention, it is understood that the methods and devices disclosed herein can be used for other viruses and pathogens.

As used herein and throughout various portions (and headings) of this patent (including the claims), the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s), merely because of such reference. Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (for instance, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

One embodiment of the present invention includes an air circulation and delivery system 150 that delivers UVC treated air to an enclosure with a controlled air flow of air containing an inactivated pathogen 602 for inducing a passive immunity in humans, birds or animals breathing in the inactivated pathogen within the enclosure (see FIGS. 6-9). A schematic illustration of the enclosure is shown in FIG. 1. The enclosure 120 has an enclosure entry vent 122 through which UVC treated air enters the enclosure, circulates throughout the enclosure, exits through the enclosure discharge vent 126, and is re-circulated after loading the pathogen and neutering the pathogen. The air entering the enclosure 120 is an air source that initially enters an air intake 102 and then passes through an air circulation pathway 115 to an air conditioning unit 104, an air mover 106, a UVC disinfection unit 108, and then into the enclosure through one or more enclosure entry vents 122. Multiple enclosure entry vents may be connected to each other via an entry vent circulation pathway 124. The air source may be passed through a test chamber 110 after it passes through the UVC disinfection unit 108 to ensure Sterility Assurance Level (SAL). The test chamber 110 allows the collection of samples to ensure absence of any active pathogens.

Another embodiment of the present invention includes a system for immunizing humans 720, birds and animals (such cattle 820, pigs 920, or chicken 1020) with an inactivated or neutered pathogenic source 602. Other embodiments include a method of providing infection control and immunization by breathing previously "treated" and neutered pathogen laden air in a closed enclosure.

Presently, infection control is provided through injections, inhalants, skin surface applications, or through agents taken by mouth. The present invention discloses a method of providing infection control by merely breathing previously "treated" pathogen laden air in a closed room or a confined environment. As described herein, the immunization method involves introducing antigens from inactivated pathogens into the air that humans, birds or animals are breathing. The antigens enter the recipient's air passages and body through normal breathing invoking an immunogenic response.

Individuals moving around in buildings, especially in nursing homes and hospitals, are exposed to viruses from infected persons. According to an embodiment, the modification of the air conditioning system in the buildings to circulate air through a UVC chamber can inactivate or neuter viruses or other pathogens in a manner that leaves their antigens still intact for generating an immune response. Thus, recirculating these inactivated pathogens with their antigenic determinants can function to stimulate immune response in animals that are susceptible to illnesses in the future resulting from infection with the live/active pathogen.

The air conditioning unit may be modified to include a UVC disinfection unit 108 in communication with the A/C unit. Healthcare workers and the uninfected persons in these facilities can be protected from the virulent pathogen when they breathe the air containing the inactivated or neutered pathogen. The same benefit can apply to other buildings, as well as, airplanes, trains, ships, etc.

The SARS-COV-2 virus 350, as illustrated in FIG. 3B, is used as an exemplary virus for discussing the embodiments of this invention. According to an embodiment, the SARS-COV-2 virus is passed through one or more UVC disinfection units where it gets neutered (inactivated) and unable to replicate in the cells of the victims. It is also possible for the spikes of the neutered SARS-COV-2 to engage the ACE2 proteins and deny the pathogenic SARS-COV-2 virus a landing site, if the spikes are not deformed or destroyed in the neutering process.

By titrating the UVC dose, pathogen is completely neutered and one or all antigens are preserved in the neutered pathogen population. The load of pathogen in the ambient air is now inactivated and cannot cause infection when it is recirculated into the buildings, airplanes, trains, etc. where the disinfected air contains the antigens. The individuals moving around in or occupying these facilities breathe the antigen-loaded air and will be immunized against future exposure to the antigenic laden pathogen.

Alternately, immunization enclosures can be created to provide the same kind of protection to individuals. Here also, the individuals sitting in or moving around in such enclosures will get immunized by just breathing the treated air containing neutered pathogens with one or more antigens. Typically, such enclosures will have a pathogen loading inlet 710 where a predetermined quantity of pathogen (i.e., the pathogen load) is injected into the system and taken through an air conditioning unit followed by a UVC disinfection unit which inactivates or neuters the pathogen without destroying its antigenic proteins/peptides. This treated air is then routed into the enclosure where one or more individuals/animals are immunized.

Air Conditioner System

As used herein the term "air conditioner system" or "air conditioning system" refers to a system that controls the temperature of the air leaving the system. The temperature is typically controlled by a thermostat. An air conditioner system may include both a cooling mechanism and a heating mechanism.

Figure 6:
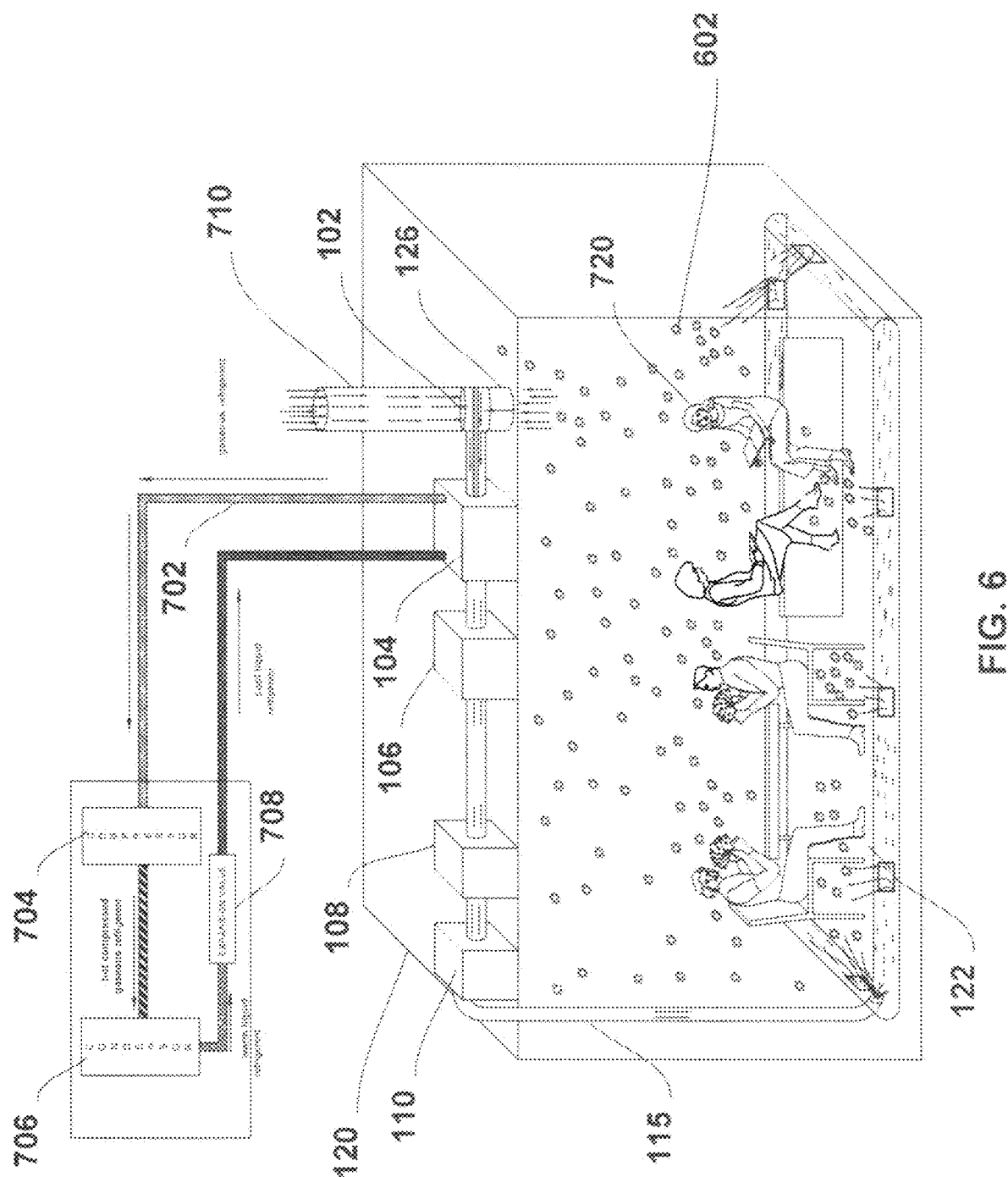
FIG. 6 illustrates humans within one embodiment of an immunization enclosure where an air delivery system circulates air laden with inactive pathogen from an enclosure entry vent to an enclosure air discharge vent.
Figure 7:
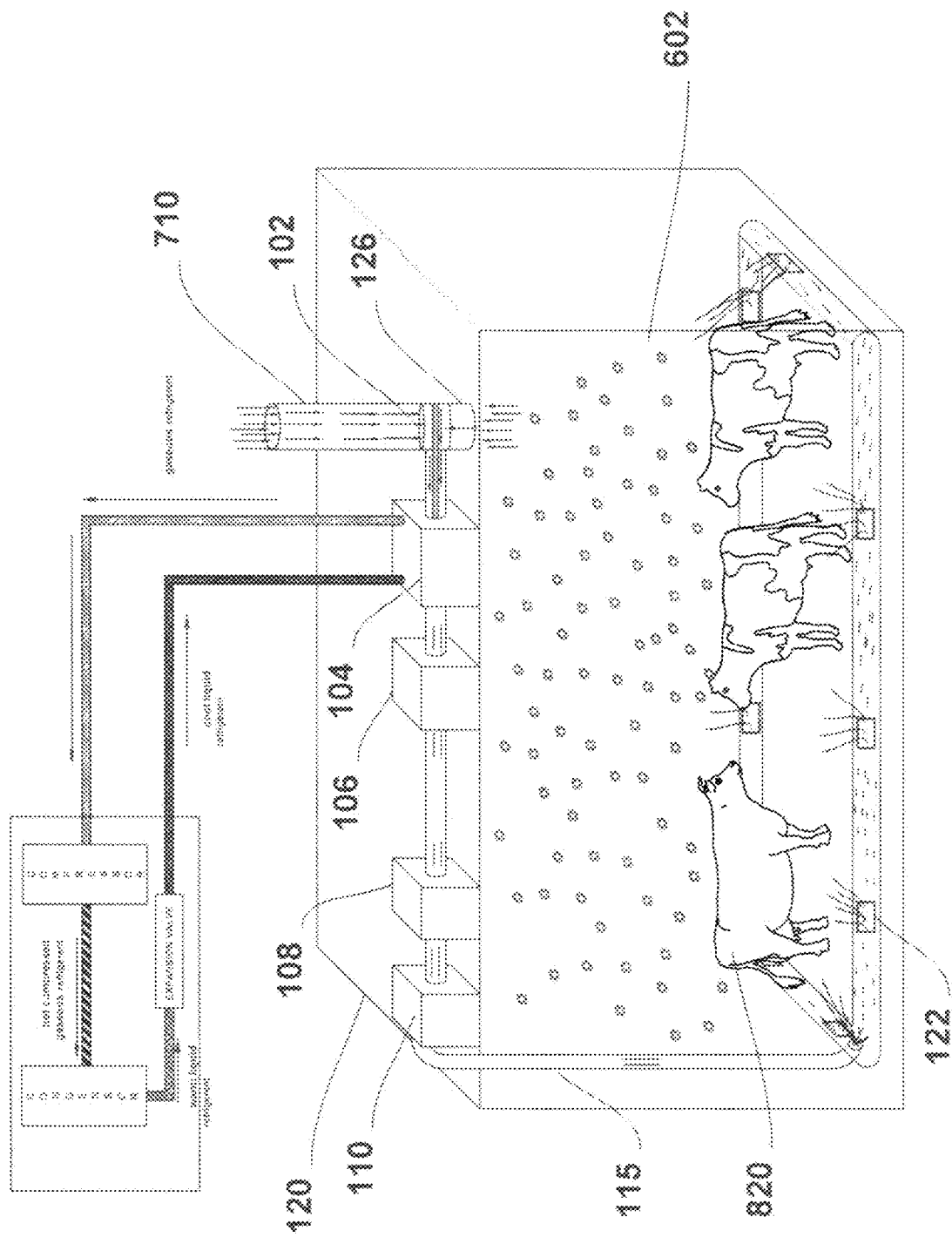
FIG. 7 illustrates cows within one embodiment of an immunization enclosure where an air delivery system circulates air laden with inactive pathogen from an enclosure entry vent to an enclosure air discharge vent.
Figure 8:
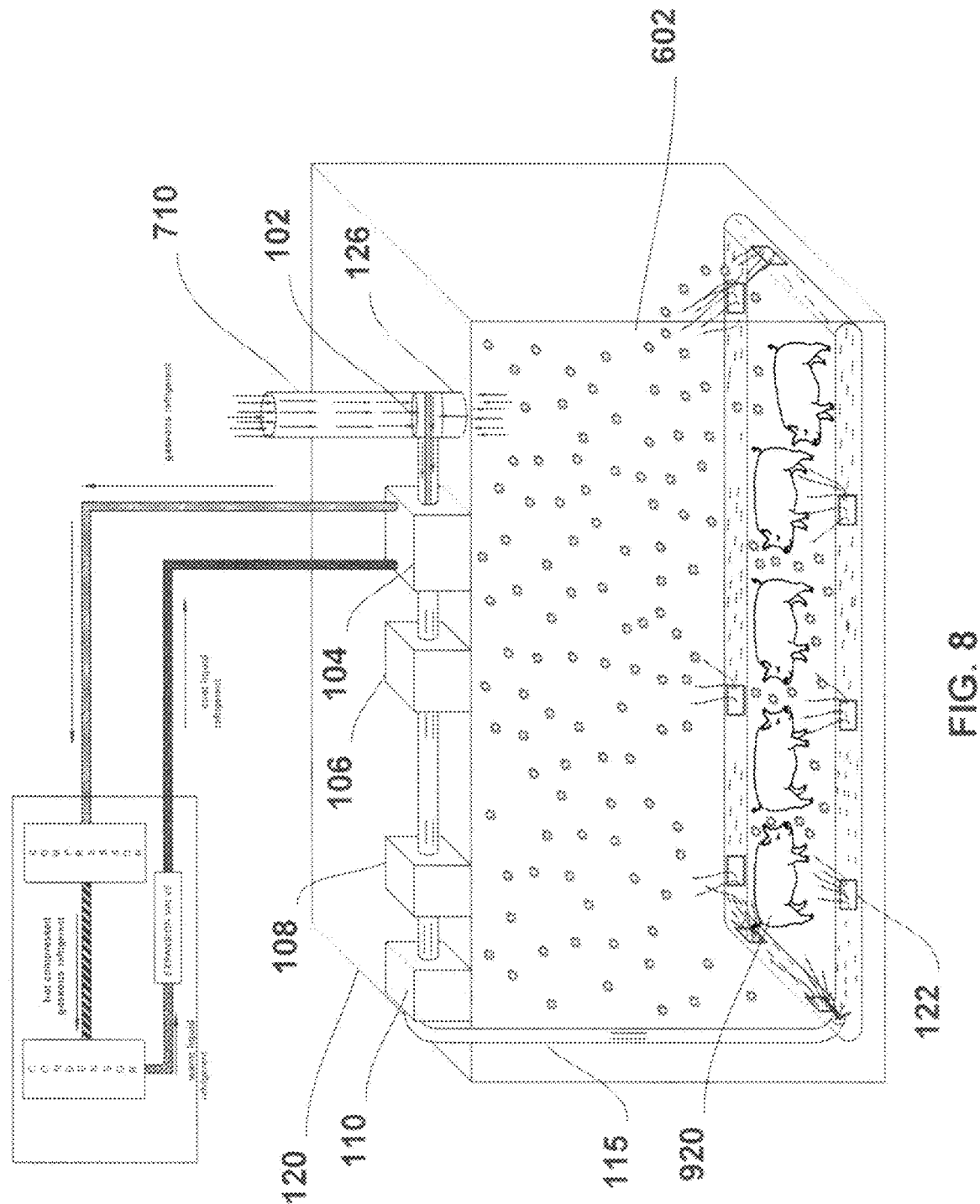
FIG. 8 illustrates pigs within one embodiment of an immunization enclosure where an air delivery system circulates air laden with inactive pathogen from an enclosure entry vent to an enclosure air discharge vent.
Figure 9:
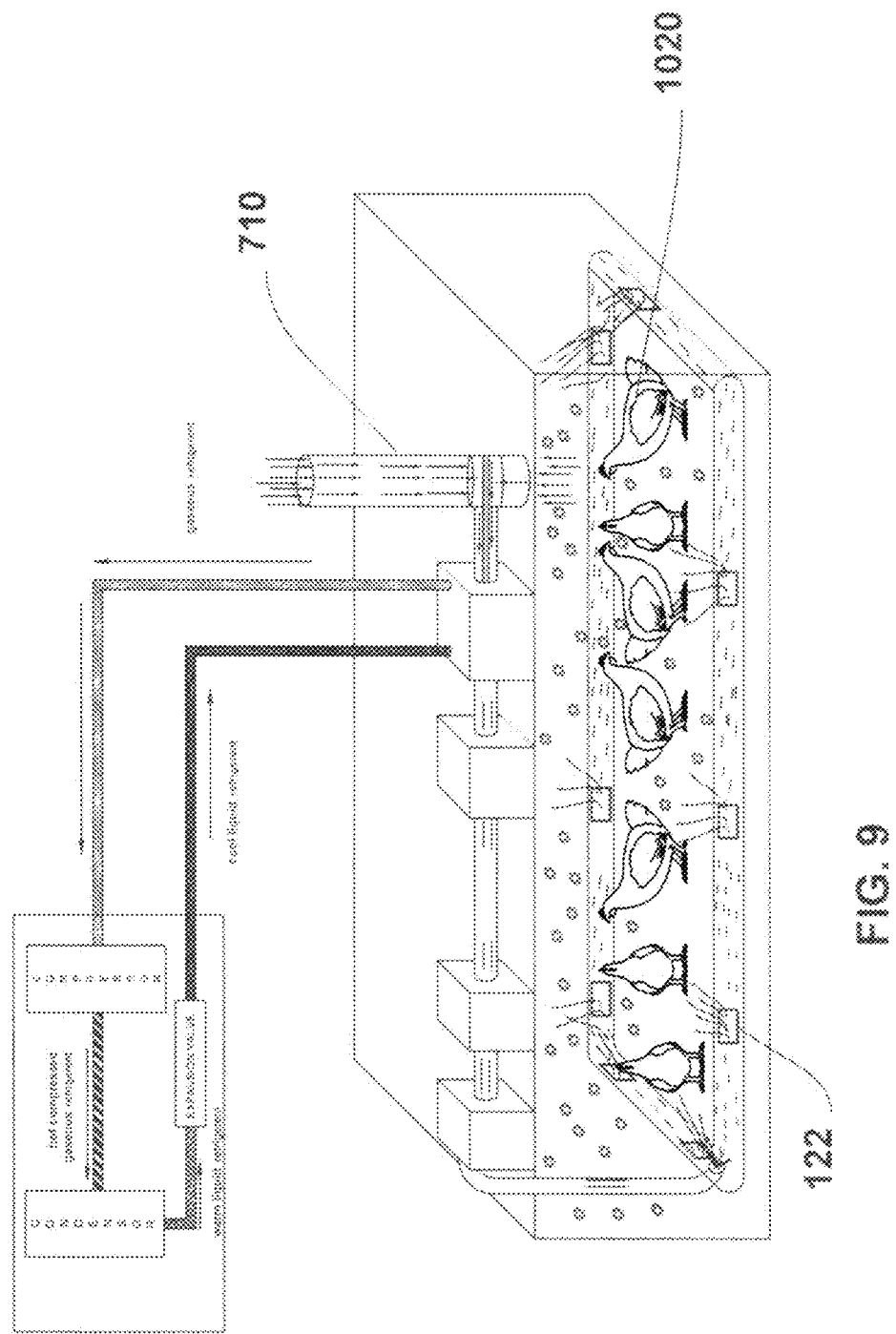
FIG. 9 illustrates chickens within one embodiment of an immunization enclosure where an air delivery system circulates air laden with inactive pathogen from an enclosure entry vent to an enclosure air discharge vent.

A schematic of an air cooling unit of the air conditioner system 104 is shown in FIG. 6. A refrigerant enters the cooling unit through an air pathway 702. The compressor 704 of the cooling unit compresses the refrigerant vapor and moves it towards the condenser 706. The heat of compression raises the temperature of the refrigerant vapor causing it to be a high pressure superheated vapor. The condensed refrigerant then moves through the expansion valve 708 that expands the refrigerant reducing its temperature before returning to the air conditioning system.

Air Mover

The air delivery system of the present invention relies on an air mover 106 or air circulator, such as an air pump or a fan, to ensure a controlled rate of air flow through the air delivery system. The rate of air flow through the system is important to the operation and efficiency of the system.

UVC Disinfection Unit

Figure 2A:
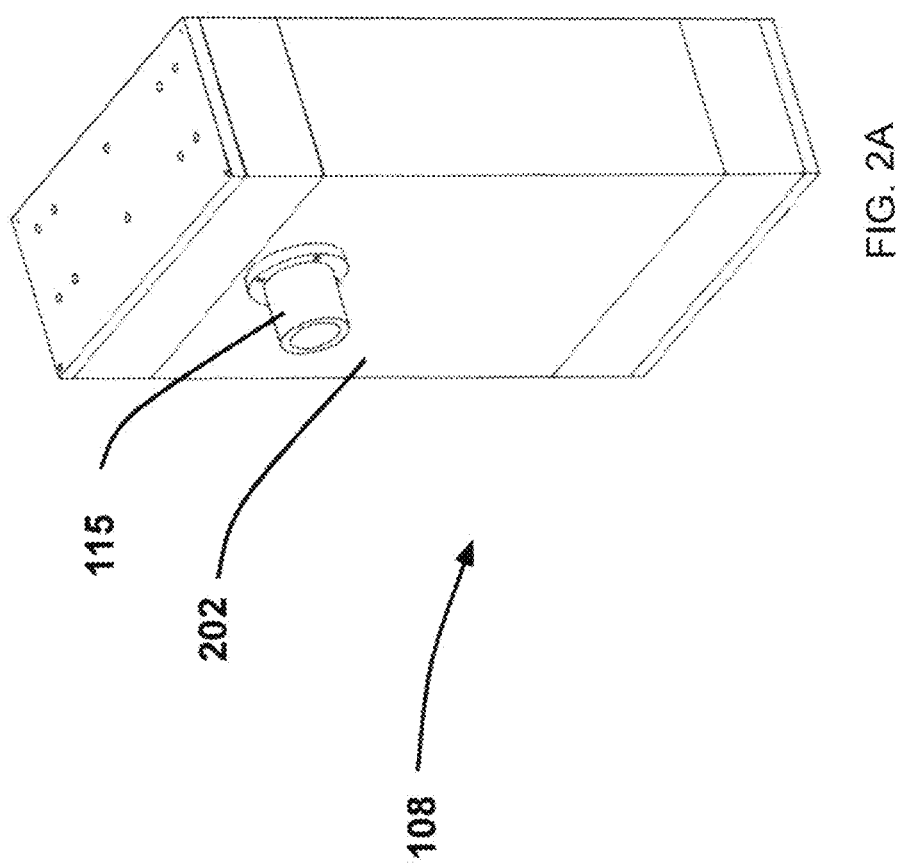
FIG. 2A illustrates one embodiment of a housing of a UVC disinfection unit.
Figure 2B:
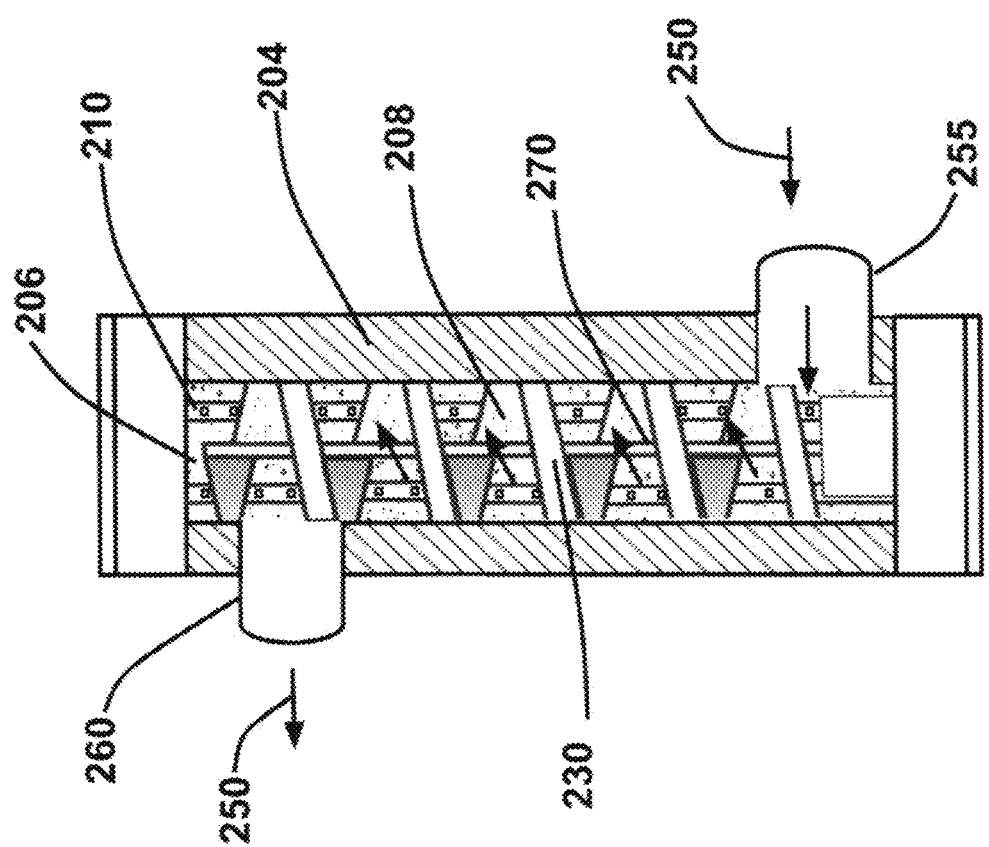
FIG. 2B illustrates one embodiment of a disinfectant chamber of the UVC disinfection unit illustrated in FIG. 2A.

One embodiment of a UVC disinfection unit 108, illustrated in FIGS. 2A-2B, has an opaque housing 202 containing one or more disinfectant chambers 206. The disinfection chamber has a chamber wall 204. The housing 202 may serve as the chamber wall, if the UVC disinfection unit 108 contains only one disinfection chamber 206. However, the chamber wall may also be UVC transparent as is often the case when the UVC disinfection unit contains more than one disinfectant chamber 206. Each chamber has a chamber inlet 255, a chamber outlet 260, and a centralized inner bore/stem 270 having an interior chamber surface 208 facing the inner bore; a UVC light source 210 positioned adjacent the interior surface; and a helical air flow diverter 230 centralized within the inner bore proximal to the UVC light source, wherein the helical airflow diverter creates a helical airflow path 250 for the air flowing through the chamber.

Each chamber will have at least one UVC light source 210 and a helical air flow diverter 230 as described above. The chamber inlet 255 allows the incoming air to enter the disinfection chamber at one end of the helical air flow diverter 230 and circulate around each rung of the helical air flow diverter until the outgoing disinfected air exits out the air outlet 260. Typically, the helical air flow diverter fills most of the empty space in the disinfection chamber thereby creating an air flow path that circulates around each helical rung in a narrow space between the disinfection chamber wall 204 and the helical air flow diverter rungs. Thus, as the air flows from the inlet to the outlet, it circulates close to the UVC light source(s) throughout the disinfection chamber(s). The particles including the pathogens in the air are driven very close to the UVC source due to the centrifugal force.

The helical air path through each disinfection chamber 206 will extend the time that the air is exposed to the UVC light sources. The time the air spends in the disinfection chambers is further controlled by the speed of air movement through the chambers as controlled by the air mover 106. The air mover controls the movement of the air through the air disinfection units. The air mover functions at different power levels that can be electronically controlled. By altering the power level of the air mover, the air circulation can be made faster or slower. The velocity of the air flow through the disinfection unit(s) will proportionately increase or decrease the dosage of UVC encountered by any pathogen in the air flow through the disinfection unit(s).

Ultraviolet Inactivation of Pathogens

UVC light is a well-known disinfectant. Many UVC light emitting devices are available in the marketplace. These devices are used to "sterilize" surgical suites, airports, and other such spaces. However, for effective disinfection, the UVC light has to be strong enough to destroy the microorganisms within a close proximity. Additionally, the microorganisms have to be exposed to the UVC light for a sufficient duration of time before they are neutralized. Such high energy UVC radiation and long exposure to UVC radiation can injure normal human cells like skin, cornea, and other cells. Therefore, UVC light should not be allowed to come near hands, face or other areas of the skin. Furthermore, exposure of the skin to UVC radiation can cause skin irritation and other ailments.

UV light is an electromagnetic radiation beyond the wavelength of the visible violet or beyond the spectrum that the human eye can see. The UV light itself has a spectrum ranging from 100 nanometer to 400 nanometers. UV light having wavelengths from 315 nm to 400 nm is called UV-A, from 280 nm to 315 nm is called UV-B, and from 200 nm to 280 nm is called UVC. Far UVC light has a spectrum ranging from 207 nm-222 nm. For the purposes of this application, the terms "UVC" and "far UVC" are used interchangeably.

The earth's ozone layer blocks the UVC but allows UV-A and UV-B to reach earth. The shorter the light wavelength is, the less it will penetrate human skin. UV-A and UV-B can damage human skin and are the ones implicated in sunburn, skin cancer, and an increased risk of cataracts. UVC from the sunlight cannot normally reach the earth because it is filtered out by the earth's ozone layer. Far UVC and UVC light penetration into the skin is low, but is sufficient to cause some major damage due to the high energy level. However, UVC light in the appropriate dosage penetrates microorganisms and denatures their RNA and/or their DNA, making the reproduction of those microorganisms impossible.

The kill rate of UVC light depends on the specific microorganism you are trying to destroy as well as the UVC dosage the organism receives. Dosage (J/m2) is a combination of exposure time and intensity (microwatts per square centimeter). $UV\_dose = UV\_bulb\_power * Exposure\_time / (4 * pi * UV\_bulb\_distance^2)$. The intensity is a measure of the power of the UVC and its proximity to the organism, where Intensity, $E = UV\_bulb\_power / UV\_bulb\_distance^2$.

There are numerous ways to control the delivery of ultraviolet light to pathogens. One controllable delivery method is to employ one or more embodiments of the unique UVC disinfection unit 108 described below.

UV Light Source.

The number, type, strength and the placement of the UVC lights 210 in the disinfection chamber 206 will ensure that all microorganisms such as bacteria and viruses in the air flow passing through the disinfection chamber will receive a sufficient UVC dosage to kill any microorganisms in the air. Likewise, the number, type, strength and the placement of the UVC lights in each disinfection chamber 206 will ensure that the bacteria and viruses in the air flow passing through the disinfection chamber will receive a sufficient UVC dosage to disinfect the air flowing through the device.

The UVC light source 210 can be any type of UVC light source, such as the UVC tubes or the UVC light strips. UVC light sources may include mercury lamps, fluorescent tubes, pulsed xenon lamps, excimer lamps, UVC LEDs, and UVC lasers. Once the UVC light source is selected and the wattage or irradiance is known, the exposure time to achieve the desired dosage can be calculated and the appropriate time for the air path to spend passing through the disinfection chambers in close proximity to the UVC lights can be determined. In fact, when more than one disinfection chamber is used, different UVC light sources may be used in the different chambers. Different UV light sources may be selected for the different wavelengths that they produce, their different intensities, their different lifespans, the difference in their heat production, or for any other reason.

Controlled Dosage.

The UVC air disinfection unit described above is a reliable means of delivering a set dosage of UVC to a pathogen in an air supply that passes through the unit. The dosage can be varied by controlling the intensity of UVC put out by the UVC source(s), the number and position of the UVC sources, the number of disinfection units and/or the number of disinfection chambers per disinfection unit. The dosage can also be varied by controlling the exposure time by varying the air flow velocity through the disinfection unit(s) or controlling the length of the air stream pathway through the unit. Examples of other variations include: varying the strength of the UVC sources, varying the proximity of the microorganisms in the air flow to the UVC sources, varying the distance traveled by the air stream, and varying the time and proximity that the air steam is exposed to the UVC light sources in the disinfection chambers 206 within UVC disinfection unit 108.

Quantitating the Damage to a Pathogen.

Aerosolized samples of a known quantity of a virulent pathogenic source will be collected before and after UVC treatment in the UVC disinfection unit(s). By choosing the appropriate wavelength of the UV radiation, it is possible to destroy the genetic material of the pathogen (i.e. DNA or RNA) before it destroys any other molecules in the pathogen. A neutered pathogen is defined herein as a pathogen with its genetic material (i.e., its RNA or DNA) destroyed so that it cannot reproduce and yet has some or all of its membrane or structural proteins intact. For instance, a ribonucleic virus can be neutered by destruction of its RNA using UVC in a dose related manner Using a minimal UVC dosage for destroying its genetic material allows the virus to retain its morphology and the structural integrity of its proteins. A vaccine derived from an intact neutered virus can generate antibodies to various antigenic regions available in one or more of the viral proteins.

Using the SARS-COV-2 virus as an example, aerosolized samples collected before and after they are subjected to a set dosage of UVC radiation will be analyzed to compare the integrity of the samples' RNA and proteins to the known structure of the virus' known RNA and proteins using standardized laboratory techniques such as 2D gel electrophoresis. One embodiment of this process sends one aerosolized standardized SARS-COV-2 viral source through each of a variety of UVC disinfection units that vary in the dosage of UVC delivered to the viral source. Samples from each UVC disinfection unit will be collected by an automatic sampling apparatus and analyzed for the integrity of the various viral components such as its RNA and proteins. Current studies show that UVC inactivation is more precise than the overall damage done to the pathogen with detergents, formalin, chlorine and other such chemicals. It is hypothesized that the resulting protein antigen is healthier after UVC neutering compared to the overall mutilation created by other agents. This is very similar to precision bombing with UVC and cluster bombing with other agents.

Numerous samples of the aerosolized standardized virulent pathogenic source will be subjected to gradual increases in UVC dosages or subjected to UVC of different wavelengths. With each incremental dosage increase or different wavelength the UVC treated pathogenic source will be collected and analyzed for any damage to the genetic material and/or proteins and compared to the untreated pathogenic source. Thus, any damage to the genetic material and/or proteins of the pathogenic source can be correlated to increases in the UVC dosage used or variations in the wavelength of the UVC to treat the pathogenic source. For example, any damage to the genetic material and/or proteins of a standardized SARS-COV-2 source can be correlated to increases in the UVC dosage of 254 nm used to treat the SARS-COV-2 virus or one with the UVC 222 nm or any other wavelengths. This information can be used to devise a method of neutering the COVID-19 virus without destroying its structure, including the nucleocapsid protein or its envelope proteins (the M protein, E protein and S protein). If the spike morphology is retained after UVC treatment, then it will continue to be able to engage SARS-COV-2 ACE 2 receptors and competitively inhibit the untreated virus's ability to engage the same ACE 2 receptors.

Other embodiments will vary the UVC dosage given to an aerosolized standardized SARS-COV-2 viral source by sending the viral source through a series of disinfection units that vary in the number or type of their UVC sources and/or disinfection chambers, or by sending the viral source through the disinfection unit(s) at different velocities or flow rates. The dosage of UVC delivered to the viral source is calculated and the degree of damage to the virus is quantified from samples collected by an automatic sampling apparatus and analyzed for the integrity of the various viral components such as its genetic material (RNA or DNA) and its proteins.

Immunogenic Compositions.

The present invention includes a process for producing an immunogenic composition. An immunogenic composition as defined herein is a neutered/inactivated pathogen that retains at least one antigenic determinant available for binding. The process comprises standardizing a known quantity of a virulent pathogenic source; determining the degree of ultraviolet inactivation of the pathogenic source required to neuter the pathogen while retaining the integrity of at least one antigenic determinant; preparing an immunogenic composition to produce or increase a person's immunity to the inactivated pathogenic source.

One embodiment of the present invention is a process for destroying the RNA or DNA of a pathogen, such as a virus, using germicidal UVC radiation. For instance, the SARS-COV-2 virus can be neutered by destruction of its RNA using UVC in a dose related manner. This allows the virus to retain its morphology and the structural integrity of its nucleocapsid and envelope proteins. To date the major SARS-COV-2 vaccines have been prepared to create antibodies to one or more portions of the S protein. However, the S protein has multiple domains. For example, if the vaccine is made only against the Receptor Binding Domain (RBD) of the S protein, the antibodies produced are only against one or two peptide portions of the S protein. As the virus continues to mutate, one or more of these mutations will eventually overcome this RBD vaccine.

Viruses rapidly reproduce in infected cells and often at least a few of the released virus particles will have mutated. Over time some of these mutations may be able to evade the antibodies made to an attenuated virus or to a portion of a protein used as an antigen in a vaccine. For example, SARS-COV-2 is an RNA virus. Typically, the SARS-COV-2 virus will try to evade the antibodies produced by a vaccine to one or more antigens used in producing the vaccine. However, the SARS-COV-2 has three envelope proteins and the nucleocapsid protein around the RNA. If each of these proteins generated one or more antibodies, then it would be harder for the virus to mutate enough to avoid all of the antibodies produced. The mutation of the virus to evade all of the antibodies produced to a variety of proteins will be difficult. This is because mutation is sustained and propagated only through progeny. If the mutation does not generate progeny, that particular mutation is discarded. In time, the virus will continue to try and mutate, but will then have to stop. Thus, vaccine evasion by a multi-mutated virus will be significantly reduced. Efforts to produce inactivated whole virus vaccines against SARS-CoV-2 have met with poor success. It is hypothesized here that the low success rate with this inactivated whole virus vaccine was because the conventional inactivation techniques mutilate the antigens to variant degrees. The UVC neutered antigens will be more effective.

A vaccine derived from an intact neutered virus can generate antibodies to various antigenic regions available in one or more of the viral envelope or capsid proteins providing a full spectrum of antigens capable of eliciting a full spectrum of antibodies. For example, SARS-COV-2 has several envelope proteins—the spike protein (S protein), the membrane protein, and the envelope protein in addition to the nucleocapsid protein; wherein each of these proteins can potentially independently elicit specific antibodies to one or more antigenic regions in each protein.

A vaccine derived from an intact neutered virus can generate antibodies to various antigenic regions available in one or more of the viral proteins providing a full spectrum of antigens capable of eliciting a full spectrum of antibodies. For example, SARS-COV-2 has several envelope proteins— the spike protein (S protein), the membrane protein, and the envelope protein, in addition to the nucleocapsid protein; wherein each of these proteins can potentially independently elicit specific antibodies to one or more of their antigenic regions. If antibodies are generated to antigenic regions of more than one protein, then a viral mutation to circumvent one particular antibody might remain unmutated while it tries to mutate against another antibody. For a successful mutation the virus will have to mutate against all four antigens simultaneously and this can frustrate the system. For any mutation to prevail and propagate, it has to have successful progeny. If the partial mutation does not produce progeny that particular mutation is usually discarded. In other words, not all mutations result in a new variant. In time, the virus will continue to try and mutate, but will then have to stop. Thus, vaccine evasion by the virus can be significantly reduced. A reduced rate of mutation will naturally occur through a reduced rate of infection.

SARS-COV-2 virus cannot multiply or mutate in the air but must mutate in infected cells. By blocking the entry of the virus into our bodies, the rate of mutation is automatically eliminated or reduced. The polyvalent vaccine has a better chance to do this. With four types of antibodies to evade, the chances are exponentially lower than with just one type of antibody. This is like a burglar trying to unlock four locks on a door at the same time. With any luck, the burglar will keep locking and unlocking the four locks randomly and will never get all the four unlocked at the same time. The polyvalent vaccine can provide a similar challenge to the virus. Partial S protein antibodies are even easier to evade by mutation. Imagine an S protein-lock has seven levers. The mutations have to cover all seven. If the antigenic determinant(s) are only a small part of the S protein, the antibodies produced are only against a few of these seven levers. This makes the mutation much easier.

For example, the simplest form of UVC damage to the SARS-COV-2 virus damages only the RNA leaving the envelope (capsule) and all its four proteins preserved. It is unlikely that all four proteins have the same threshold for destruction by UVC. The same is true for the structure of the envelope itself. After determining the gradation of sensitivity for destruction of viral components by UVC, one may predictably produce different levels of SARS-COV-2 damage such as RNA damage with all four proteins preserved, RNA and one protein damaged with three proteins preserved, RNA and two proteins damaged with two proteins preserved, and RNA and three proteins damaged with only one protein preserved. A vaccine can be produced from any one of these graded options and that vaccine can be tested for diverse antibody production and their risks and benefits. Thus, an educated selection can be made of which damaged virus should be included in an inoculum or vaccine. Theoretically, the first option with all four proteins preserved will have more advantages than the others provided this vaccine has no increased risk to the recipient.

The development of polyvalent neutered whole virus vaccine can be explained using SARS-COV-2 as an example. This virus has positive-sense, single strand, RNA combined with nucleoprotein as its core. This type III virus has an envelope made of two main proteins, the M (for membrane or matrix) and E (for envelope) and an "attack" protein projecting out and appropriately called the spike protein. By utilizing two-unit systems, to produce predictable, graded, optimal damage to the virus, it should be possible to produce four types of antigens. The lowest dose of UVC can just neuter the SARS-COV-2 by denaturing the RNA without damaging the architecture of the virus or the four proteins. The UVC damage is so precise that it can destroy the RNA while preserving the nucleocapsid protein that is in close association with the RNA like in a braided cord. This product will have four potential antigens from the four preserved proteins for creating a broad-spectrum antibody reaction. By increasing the strength and duration of the UVC and the proximity of the virus to the UVC right inside the first chamber/unit, a second possible product will be a neutered virus with one damaged protein. It will not be difficult to measure the sensitivity of the four proteins to UVC, and by using appropriate dose of UVC the viral antigen can be with four proteins, three proteins, two proteins and just one protein. For instance, the first housing can have UVC of wavelength 254 nm which is absorbed heavily by the nucleic acid and will be good for neutering the virus. The second housing can have UVC of wavelength 222 nm which is absorbed heavily by the proteins. Grading of the protein damage can be accomplished by adjusting the UVC 222 dosing in the second housing.

Since the RNA is denatured in all four of these products, the resulting whole virus cannot be multiplied in any cell and is not infective. It is difficult to predict which of these four UVC damaged viruses will make the optimal vaccine. This has to be determined with animal experiments and a determination of risks versus benefits. Common sense dictates that the neutered virus with four antibody-producing proteins will be the best vaccine. In this situation, the virus will have to create mutations against all antibodies at the same time to evade the vaccine. Mutations are "errors" produced during virus multiplications in the cells (accidental evolutionary, random or whatever) but not calculated or intentional. The more viruses in circulation the more chance for mutations. Such mutations take place in each infected person through each virus multiplication cycle. At the peak of COVID-19, the estimated number of mutations generated daily in the world was about 100,000 to 1 million.

A neutered SARS-COV-2 virus is like a defanged cobra. A defanged cobra can crawl into crevices and get into a house, but it cannot hurt the inhabitants without its teeth. Likewise, the neutered SARS-COV-2 virus, that retains its morphology, will invade human cells through the same ACE2 entrance gates. Then, the neutered SARS-COV-2 virus would die with no progeny. Additionally, the undamaged proteins released by the dead virus can provide foreign antigens that the body can generate antibodies against. These antibodies can then attack and defeat any future active virus invasions. The multiple antibodies produced against different components of the virus can react with the virus and negate its ability to reproduce and cause illness. Furthermore, the virus will struggle to overcome these multiple protein antibodies. Using a specialized pathogen-killing or pathogen-taming system, vaccines of these four grades can be created. The predictable graded destruction of the pathogens will facilitate the development of reliable and optimal vaccines.

A neutered, inactivated live virus vaccine provides the benefits of live vaccines without the risk of the individual getting infected. Attenuated live vaccines tend not to infect the individual; however, the live vaccine can sometimes misbehave and thereby infect an individual. The neutered SARS-COV-2 vaccine is better than inactivated whole virus vaccines as it does not have any side effects from the agents used to inactivate the virus. Also, the virus and its capsid or envelope proteins are not mutilated in the process of neutering it, unlike in the process of inactivating the virus using other methods. The UVC treated neutered non-mutilated SARS-COV-2 virus behaves like the whole virus in its antigenic potential without any side effects and without causing any infection by accident.

It is a known fact that most of the human pathogens are transmitted to humans from the original sources from birds, bats, chimpanzees etc. One of the methods to reduce human infection is by controlling the infection in the animals, birds, bats etc. by vaccinating them and isolating the infected ones this may serve as an alternative to sacrificing a large population of cattle, chicken etc. and can save lives as well as money. For instance, an avian flu outbreak has been reported in the United States of America as of Jan. 4, 2024 and about 1 million chicken have been euthanized. This infection can also rarely cross over to humans. Similarly, in April of 2009, Egypt killed all its 300,000 pigs to control swine flu. The humane slaughter association helps to determine when cattle, sheep, goat, pigs, deer, and poultry need to be subjected to emergency killing to prevent spread amongst them as well as spread to the humans this can cause economic hardship in addition to other problems.

Delivering Immunogenic Compositions

Embodiments of the present invention include methods for immunizing people and other animals with an inactivated or neutered pathogenic source. One example of a neutered pathogenic source may be a SARS-COV-2 virus that is neutered with a defined dose of UVC light. Presently, immunizations are provided through injections, inhalants, skin surface applications, or through agents taken by mouth. The present invention discloses a method of providing infection control/immunization passively, that is through contactless means, by merely breathing in an inactivated or neutered pathogen having exposed antigens. The antigens enter the recipient's air passages and body through normal breathing. The recipients that breathe in the inactivated pathogen with its antigens exposed will make antibodies to various antigenic determinants within those exposed antigens.

Figure 5:
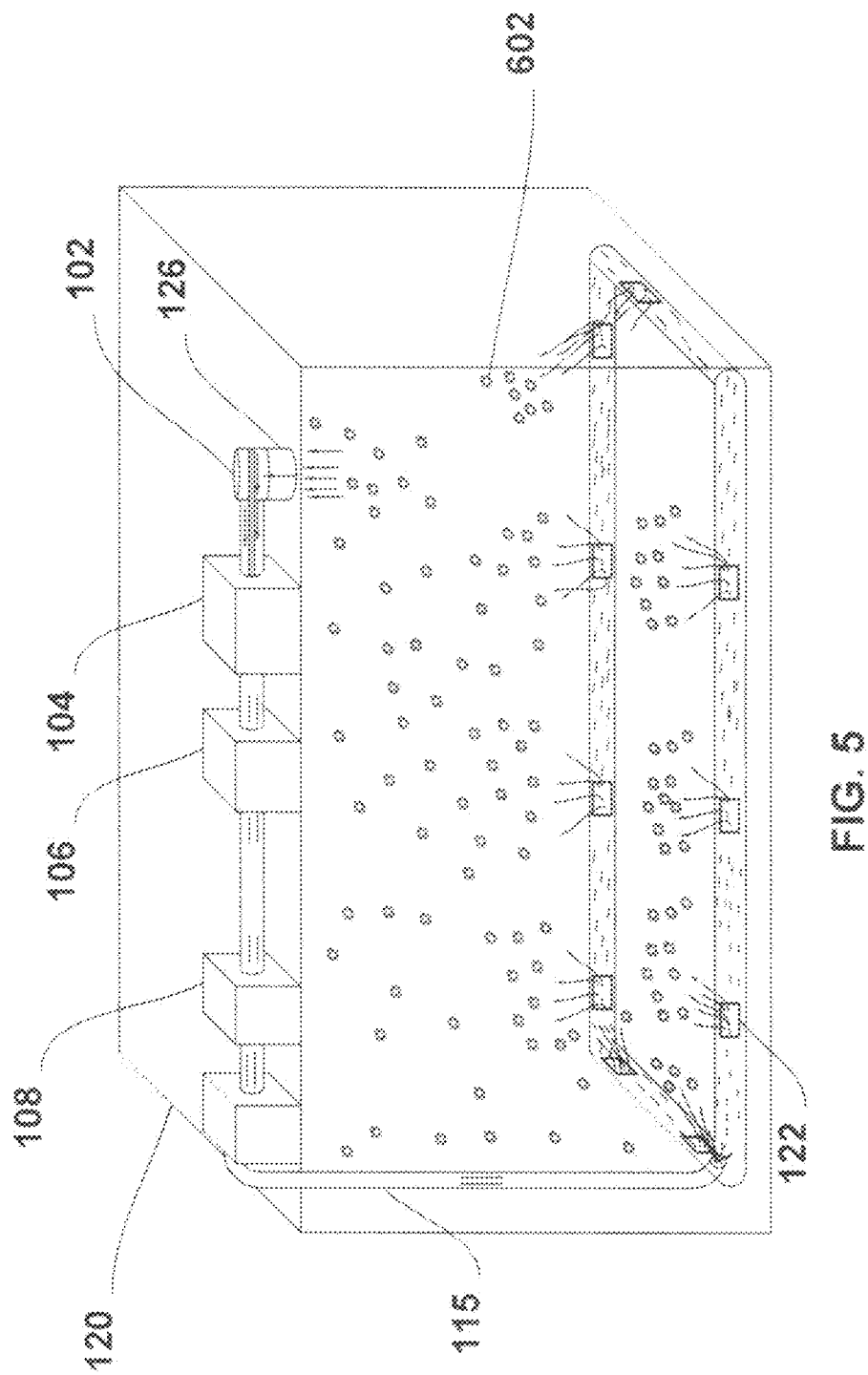
FIG. 5 illustrates one embodiment of an air delivery system showing the air laden with inactive pathogen in an enclosure going from an enclosure entry vent to an enclosure air discharge vent.

Inactivated pathogens 602 having their antigens exposed may be presented to a person via a previously "UVC treated" ambient air in a closed room or a confined environment 120 such as shown in FIG. 5. As described herein, the UVC treatment of air involves the inactivation of pathogens in an air source. The pathogens may be those intentionally introduced at a precalculated dose, or those from viruses or pathogens released into any given air source by people and animals that have shared that air source.

Advocates of inhalation vaccines, such as those described herein, have highlighted that they promote both a mucosal immune response as well as a systemic immune response. A vaccination that is introduced by normally breathing treated air is easier to dispense and more likely to be accepted as they will not cause patient discomfort.

For example, SARS-COV-2 virus enters the body through the upper airways and spreads to the rest of the body. More specifically, the rear two thirds of the nasal passage is known as the landing place for this virus. This is why one swabs the rear portion of their nasal passage for a proper diagnosis of this virus. By providing a vaccine that can be inhaled and deposited along of the nasal passage, the attack on the virus is focused at its first landing place and will be more effective. This will also ensure that the neutered and artificially created "pseudo virus" will engage all the ACE 2 entry points on the host cells making the true virus particles lost in the wilderness with no ACE 2 entry points in the upper respiratory tract.

COVID-19 researchers have attempted to improve the systemic immune response and the mucosal immune response. Advocates of inhalation subunit vaccines have highlighted this as an additional benefit of inhalation vaccines. Promoting both a mucosal immune response and a systemic immune response may be achieved by a total viral protein vaccine and will perform better than the subunit vaccines currently undergoing clinical trials.

Contained Spaces with Treated Ambient Air. Some embodiments of the invention include methods of providing infection control/immunization by merely breathing previously "treated" ambient air in a closed room or a confined environment.

Figure 4:
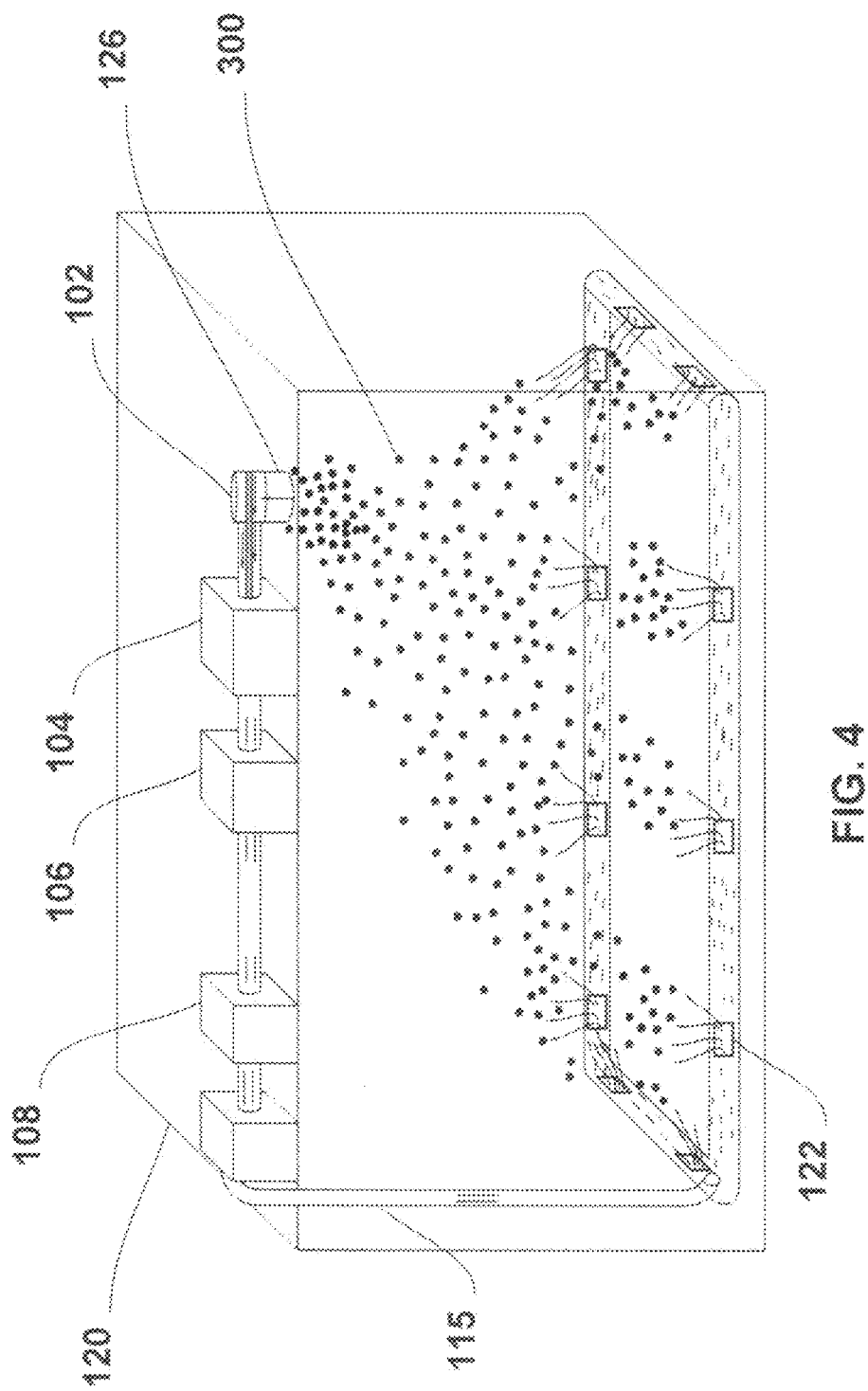
FIG. 4 illustrates one embodiment of an air delivery system showing the air circulation laden with active pathogen in an enclosure going from an enclosure entry vent to an enclosure air discharge vent.

Individuals moving around in buildings, especially in nursing homes and hospitals, are exposed to circulating air borne pathogens 300 (see FIGS. 3A and 4), such as the COVID-19 virus 350 (illustrated in FIG. 3B). Typically, the viruses and other pathogens released into the air of a room or enclosure by other people that have occupied that space are recirculated evenly throughout the room as shown in FIG. 3A or unevenly as shown in FIG. 4 by the commonly available air conditioning systems. According to an embodiment shown in FIG. 6, the modification of the air circulating and conditioning system in rooms or buildings that circulate a room's air supply through a UVC disinfection unit 108 can inactivate or neuter viruses or other pathogens 602 in a manner whereby the pathogens retain their antigenicity. Such inactivated pathogens can function as a immunogenic composition to stimulate an immunogenic response.

The modified air circulation and delivery system 150 can include a self-cleaning circulation system with one or more UVC disinfection units 108 in the air circulation system. Each disinfection chamber 206 with its UVC lights 210 and helical airflow diverter 230 irradiates the air flowing through the chamber. The air disinfection unit 108 may be configured with various different dimensions as selected to fit the needs of a particular embodiment of an enclosure such the embodiment shown in FIG. 1. A test chamber 110 is incorporated into the modified air delivery system 150 where one can selectably remove a sample of the treated air to test the sample and make sure that the pathogen is totally neutered and for the presence of available antigenic determinants For example, if the SARS-COV-2 virus is taken up into the system 150 the SARS-COV-2 virus is passed through one or more UVC air disinfection units 108 where it gets neutered (inactivated). By titrating the UVC dosage, one or all of the SARS-COV-2 antigens are preserved in this neutered virus population. The load of virus in the ambient air is now inactivated and cannot cause infection when it is recirculated into the buildings, airplanes, trains, etc. where the disinfected air contains the antigens. The individuals moving around in or occupying these facilities breathe the antigen-loaded air and will be immunized against exposure to the antigenic laden pathogen. Other viruses or pathogens may also be inactivated and serve as a vaccination against those viruses or pathogens. This is similar to allowing the children to spend time outdoors to develop a stronger immune system and resistance to allergens.

As shown in FIGS. 6-9, the enclosure can be provided as a free-standing or stand-alone immunization enclosure to provide immunization to humans or animals. The free-standing enclosure can be conveniently transported to a desired location. In one or more embodiments, the free-standing enclosure can be configured as a mobile or transportable unit.

As shown in FIG. 6, the free-standing enclosure can be configured to provide protection to one or more individuals against specific viruses or pathogens within those enclosures. The same arrangement can be used to immunize cattle (FIG. 7), pigs (FIG. 8), birds (FIG. 9) or other animals. Here, the individuals sitting in or moving around in such enclosures will get immunized by just breathing the air in the enclosure. Such enclosures may be modified to include multiple enclosure air entry vents 122 at various heights and various locations to ensure adequate circulation throughout the enclosure. Such an immunization enclosure may be set up to accept a known quantity of a pathogenic source through air intake 102. An air mover 106 will move the pathogenic source from the air intake 102, through a UVC disinfection unit 108 which inactivates or neuters the virus without destroying the antigenic proteins. This treated air is then routed into the test chamber 110 where the treated air can be sampled to make sure that the pathogens are totally neutered before it is circulated throughout the immunization enclosure.

Typically, the immunization enclosure is designed for an average healthy population that would qualify for a standardized vaccination dose. There will be individuals that are outliers who will not be suitable for this kind of simple immunization. Those individuals will have to be treated separately. The immunization enclosures have at least two major variables. One is the pathogenic dosage fed into the system and the other one is the duration of time that the individual(s) stay in the chamber. Typically, the pathogenic dosage fed though the air intake is inversely proportional to the duration of time for people to stay in the enclosure.

Personal Bio-Protective Device (PPBD). Some embodiments of the invention administer the aerosolized inactivated or neutered pathogenic source through a portable personal bio-protective device (PPBD) 1125. One embodiment of a PPBD is shown in FIGS. 10A and 10B. The illustrated embodiment of the PPBD is portable and is designed to be worn or carried by an individual 1120 during use.

The PPBD has a central air disinfection unit 1110, with many features similar to that illustrated in FIGS. 2A-2B and described above. The embodiment shown in FIG. 10A has a single disinfection chamber 1203 fitted into a UV impenetrable housing 1202 that has an air inlet 1255, an air exit 1256. The disinfection chamber 1203 has a transparent chamber wall 1206, a chamber inlet 1260, active virus feeding port 1010, a chamber outlet 1262, and a helical air flow diverter 1230. The air moves through the disinfection chambers 1203 in a serpentine manner Take for example the passage of a pathogen laden sample through the disinfection chamber 1206. The air enters at the chamber inlet, circulates around the helical air diverter, out through the chamber exit, and into an adjacent disinfection chamber if the PPBD has more than one disinfection unit.

The chamber air exit 1256 is connected to an air tubing or passage 1270 that is connected to an air mover 1104. The air mover pulls air 1108 from the air inlet 1255, through the disinfection chambers 1203, into the air passage 1270, through the air mover 1104, and out of the disinfection unit through an optional test chamber 1106, through a tubing 1112, and into a face mask 1115. The air mover is powered by a power unit 1102. The air mover governs the air flow velocity through the disinfection unit 1110 thereby controlling the time spent within the air disinfection chamber(s).

A known quantity of a pathogenic source, as described above, may be sent through the air inlet 1255 and is disinfected or neutered as it flows through the disinfection unit. An optional test chamber 1106 between the air disinfection unit 1110 and the face mask 1115 allows the disinfected air exiting the disinfection unit to be tested for pathogenic activity before it is delivered to the face mask 1115 and the person 1120 wearing the face mask. The disinfected air is delivered to an individual who will be exclusively inhaling air within the face mask. When the person wearing the mask breathes in the treated air, the antigens of the disinfected or neutered pathogen enter the person's air passages and initiate that person's immune responses and their production of antibodies to fortify that person against future infection from that pathogen.

Thus, a known quantity of SARS-COV-2 virus or a similar virus can be injected through an input port into the disinfection unit 1110 where it is inactivated. The inactivated pathogen is sent to the air-tight mask 1115 where the individual is forced to take in the inactivated or neutered pathogen. The neutered pathogen is the immunogenic composition capable of inducing an immune response, and the individual takes in the composition by breathing the treated air. The dosage of the pathogen, the dosage of the UVC, etc. are calculated prior to using the disinfection unit and the PPBD. The dosage can be personalized, such as adjusting the dosage for children. A test chamber is typically incorporated to make sure that the virus is totally denatured and inactivated before it is released to go into the mask.

Some embodiments of the PPBD may be designed to be worn by an individual, see FIG. 10B, whenever that individual is exposed to enclosed areas that may have viruses or other pathogens given off by other individuals. The PPBD is designed to inactivate any virus or pathogen given off by infected persons sharing the air space with the wearer of the PPBD. The treated ambient air may contain inactive pathogens with exposed antigens that will activate the immune response of the wearer of the PPBD.

While the foregoing describes various embodiments of the invention, additional embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:

1. A system for delivering inactivated pathogens to an enclosure, comprising:
   an air delivery system, the air delivery system comprising:
   (a) an air intake;
   (b) an air conditioning unit;
   (c) an air mover;
   (d) a UVC disinfection unit;
   (e) an enclosure;

(f) an enclosure air entry vent;
(g) an enclosure air discharge vent;
(h) an air circulation pathway going from the air intake through an air duct connected at one end to the air intake and at a second end to the enclosure air entry vent that opens into the enclosure, wherein the air duct provides a passageway through the air delivery system; and
(i) a pathogen loading inlet connected to the air circulation pathway, wherein a predetermined quantity of pathogen is injected into the system.

2. The system as claimed in claim 1, wherein the air mover controls a velocity of air movement through the air duct.

3. The system as claimed in claim 1, wherein the UVC disinfection unit comprises a housing that encloses a disinfection chamber that has:
(a) a chamber wall;
(b) a chamber inlet;
(c) a chamber outlet;
(d) a centralized inner bore having an interior chamber surface facing the inner bore;
(e) a UVC light source positioned adjacent the interior chamber surface; and (f) a helical air flow diverter centralized within the inner bore proximal the UVC light source, wherein the helical airflow diverter creates a helical path for the air circulation pathway to proceed through the disinfection chamber from the chamber inlet to the chamber outlet.

4. The system as claimed in claim 3, wherein the air disinfection unit contains more than one UVC disinfection chamber.

5. The system as claimed in claim 1, wherein the enclosure is a room, a nursing home, an airplane, a train, a ship, or a critical care unit in a hospital.

6. The system as claimed in claim 1, further comprising a test chamber connected to the air circulation pathway adjacent the UVC disinfection unit.

7. The system as claimed in claim 3, wherein the air disinfection unit contains more than one disinfection chamber.

8. The system as claimed in claim 1, wherein the system is configured as a contactless system for immunizing humans, birds or animals.

9. The system as claimed in claim 8, wherein the enclosure is a free-standing, mobile enclosure.

* * * * *